United States Patent
Yamada et al.

(10) Patent No.: US 6,495,105 B1
(45) Date of Patent: Dec. 17, 2002

(54) APPARATUS FOR EVALUATING CATALYST PERFORMANCE

(75) Inventors: Yusuke Yamada; Atsushi Ueda; Tetsuhiko Kobayashi, all of Osaka-fu (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/472,097

(22) Filed: Dec. 23, 1999

(30) Foreign Application Priority Data

Dec. 25, 1998 (JP) .......................... 10-376723

(51) Int. Cl.[7] .............. B01J 35/02; G01N 7/00
(52) U.S. Cl. ................ 422/83; 422/98; 422/211; 436/152; 436/37
(58) Field of Search .................. 422/83, 98, 211, 422/89, 94–99; 356/301; 364/582; 250/373; 436/113, 37, 152; 60/274, 276

(56) References Cited

U.S. PATENT DOCUMENTS

| | | |
|---|---|---|
| 4,099,923 A | 7/1978 | Milberger |
| 5,776,359 A | 7/1998 | Schultz et al. |
| 6,004,617 A | 12/1999 | Schultz et al. |

FOREIGN PATENT DOCUMENTS

| | | |
|---|---|---|
| WO | WO 01/44801 | 6/2001 |

OTHER PUBLICATIONS

Cong, et al., "High-Throughput Synthesis and Screening of Combinatorial Heterogeneous Catalyst Libraries," Angew. Chem. Int. Ed., 38(4), pp 484–488, 1999.
Hoffman, et al., "Parallel Synthesis and Testing of Catalysts under Nearly Conventional Testing Conditions," Angew. Chem. Int. Ed., 38(18), pp 2800–2803, 1999.
Cong, et al., "Combinatorial Discovery of Oxidative Dehydrogenation Catalysts within the Mo–V–Nb–O System," Proc. Natl. Acad. Sci., vol. 96, pps 11077–11080, 1999.
Yamada, et al, "Utilization of Odor Sensor System for High Throughput Catalysts," Electrochemical Society Proceedings, vol. 99–23, Butler, et al., eds., The Electrochemical Society, Inc., Pennington, NJ, pps 143–149, 1999.
Yamada, et al., "Potential of Gas Sensor System for High Throughput Screening of Combinatorial Catalysts," *Combinatirial Catalysis and High throughput Catalyst Design and Testing*, Derouane, et al., eds, NATO Science Series, Series C: Mathematical and Physical Sciences, vol. 560, Kluwer Academic Publishers, Dordrecht, Jul. 1999.
Yamada, et al., "Quick Evaluation of Catalysts Using Odor Sensors," Catalyzer meeting ™84, p. xii, x and 248 Oct. 2, 1999. (Non English with partial translation provided).
Yamada, et al., "Combinatorial Chemistry and High Throughput Screening for Heterogenous Catalysts," Chemical Sensors, 15(3), pps 100–108, Dec. 15, 1999 (Non–English with partial translation provided).

*Primary Examiner*—Jill Warden
*Assistant Examiner*—Brian Sines
(74) *Attorney, Agent, or Firm*—Knobbe, Martens, Olson & Bear, LLP

(57) ABSTRACT

Apparatus 1 for evaluating catalyst performance according to the invention comprises a reaction vessel 2 in which a plurality of catalysts S are disposed at a distance, supply pipes 3 for supplying a reactant gas into the reaction vessel 2, a plurality of measuring instruments 7 provided with gas sensors 71 for sensing the gas formed by the contact of the reactant gas with a plurality of catalysts S, and outputting signals according to the kinds and concentrations of the formed gas, and a calculating unit 8 for receiving the output signals from the plurality of measuring instruments 7 and identifying the kinds of the formed gas and calculating the concentrations thereof. With such a constitution, performance evaluation on a plurality of catalysts can be made concurrently, quick and in simple steps.

3 Claims, 2 Drawing Sheets

APPARATUS FOR EVALUATING CATALYST PERFORMANCE

FIELD OF THE INVENTION

The present invention relates to an apparatus for evaluating the performance of catalysts by determining the kinds and concentrations of the gases formed in a reaction of starting materials in the presence of the catalyst.

PRIOR ART

To evaluate the performance of a solid catalyst in the gas phase chemical reaction, gas chromatography has been used for analyzing reaction products. The gas chromatography process comprises a gaseous mobile phase for carrying a multi-component product and a stationary phase for retaining the components of the product for separation, and separates the product into components by the differences in characteristics of each component relative to the stationary and mobile phases. The separated components are identified by a qualitative detector such as a mass spectrometer, and/or the concentrations or masses are determined by a quantitative detector such as an flame ionization detector.

Catalyst performance is evaluated by the gas chromatography, measuring the temperature of the catalyst at which the gaseous chemical reaction starts or determining the relative amounts of the useful and useless products.

The gas chromatography is an excellent method in that multi-component products can be precisely analyzed. However, it requires at least several ten minutes for a single analysis step due to theoretical restriction, and it is impossible to evaluate plural catalytic products concurrently with a single apparatus. Accordingly, on evaluation of the performance of a plurality of catalysts, it is necessary to carry out a time-consuming analysis and evaluation for each catalyst, which is extremely laborious.

Combinatorial chemistry is a procedure for developing a new material or product and is receiving attention in the field of pharmaceuticals and other functional materials. Tn the catalyst-related field, a catalyst-developing procedure which utilizes the concept of combinatorial chemistry has recently been noted. In the combinatorial chemistry, a large amount of catalyst candidate is prepared at a time and evaluated. The most important requirement in the application of the combinatorial chemistry to this field is the quick analysis and quantitative determination of the compounds formed by the catalytic reaction. Since the gas chromatography so far widely used as the procedure for analyzing the gas formed by reaction is expensive and requires relatively a long time for analysis, it cannot meet the time requirement essential in the combinatorial chemistry.

SUMMARY OF THE INVENTION

The present invention has been accomplished to solve the above drawbacks of the prior art, and an object thereof is to provide an apparatus with which evaluation of catalyst performances of plural catalysts can be made concurrently, quickly and in simple steps.

In order to attain the above object, the present invention provides an apparatus for elvaluating catalyst performance comprising:
- a vessel in which a plurality of catalysts are disposed at a predetermined distance;
- a supply device for supplying a reactant gas into the vessel;
- a plurality of measuring instruments provided with at least one gas sensor for each of the catalysts, each gas sensor detecting the formed gas individually by the contact of the reactant gas with the catalysts, and outputting signals according to the kind and concentration of the formed gas; and
- a calculating unit for identifying the kind of the formed gas and calculating the concentration thereof based on the output signal of the plurality of the measuring instruments.

Since the apparatus of the present invention brings the reactant gas into a plurality of catalysts at a time and detects the formed gas on each catalyst, it is possible to evaluate the performance of the plurality of catalysts concurrently. Further, since the gas sensors used for sensing formed gases have quick response, cheap price, and simple structure, the evaluation of performance of catalysts can be made quickly and in simple steps. Accordingly, analysis and quantitative determination of a large amount of catalyst candidate materials by combinatorial chemistry can be performed in a short time. Consequently, the catalyst development, which had hitherto required a long time, can be accelerated.

According to a preferred embodiment of the present invention, the plurality of measuring instruments are respectively provided with a plurality of gas sensors, and the calculating unit calculates the concentration of the formed gas by comparing the output values of the gas sensors taken by a preliminary measurement of a plurality of gases whose kinds and concentrations are known, with the output values of the gas sensors taken by a measurement of the formed gas.

In a further preferred embodiment of the present invention, the plurality of measuring instruments are respectively provided with a plurality of gas sensors, and the calculating unit identifies the kinds of the formed gas and calculates the concentration thereof by comparing the patterns of output values of the gas sensors taken by a preliminary measurement of a plurality of gases whose kinds and concentrations are known, with the patterns of output values of the gas sensors taken by a measurement of the formed gas.

According to the above preferred embodiment, a plurality of gas sensors are used to identify the kind of the formed gas by the comparison With the output values of the gas sensors taken by measurement of gases whose kinds and concentrations are known or by the matching with the patterns of the output values and calculate the concentration of the formed gas, analysis precision can be improved in comparison with the analysis using a single gas sensor. Furthermore, according to the present invention, the kind of the formed gas is identified and the concentration of the formed gas is calculated by the comparison with the known amount as in the pattern matching process, the analysis of the formed gas can be performed quickly.

In a further preferred embodiment of the present invention, the apparatus for evaluating catalyst performance further comprises a plurality of suction apparatuses, provided in the vicinity of each of the plurality of catalysts, for sucking the formed gas and leading the formed gas to the measuring instruments According to the above embodiment, the gas formed under each of the catalysts is sucked immediately after the formation by a suction apparatus provided in the vicinity of each catalyst, the possibility for the formed gas to be mixed with the gas formed under other catalysts and led to the measuring instrument in mixture is reduced, and the analysis precision can be improved.

The other objects and features of the present invention will become apparent from the following description accompanied by drawings. It is to be understood that the present invention is not to be limited to the following embodiments but be modifiable in various manners within the scope of the claims.

PREFERRED EMBODIMENTS OF THE INVENTION

Figure 1:
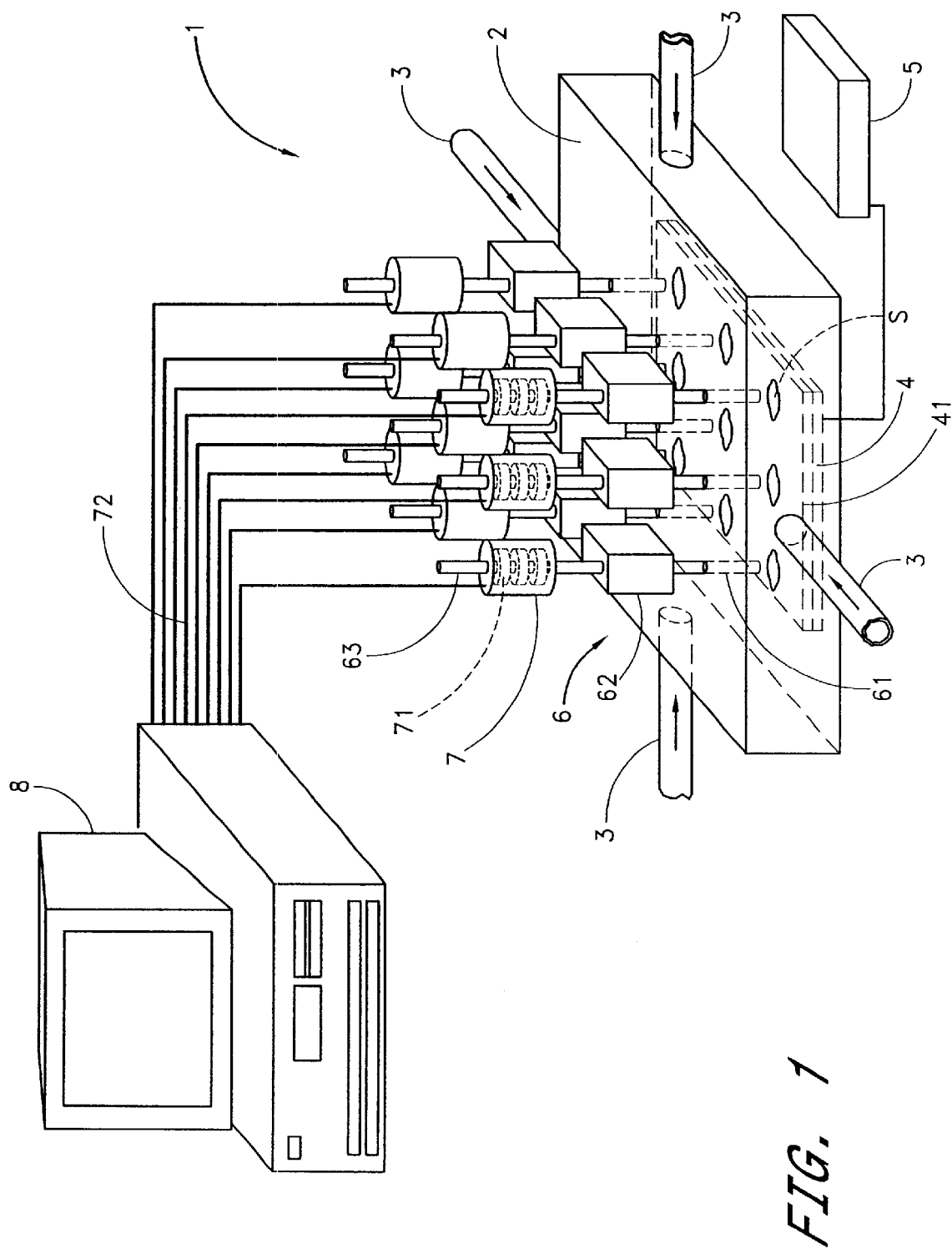
FIG. 1 shows schematically one embodiment of the apparatus for evaluating the performance of a catalyst according to the present invention.

Hereinafter, preferred embodiments of the present invention will be explained with reference to the drawings. First, explanation will be made on the constitution of the catalyst performance evaluation apparatus according to the present invention. FIG. 1 is a schematic view showing an embodiment of the catalyst performance evaluation apparatus according to the present invention. The catalyst performance evaluation apparatus 1 comprises a sealed reaction vessel 2, four supply pipes 3 for supplying reactant gas into the reaction vessel 2, a hot plate 4 for heating nine catalysts S, a temperature regulator 5 for adjusting the temperature of the hot plate 4, nine suction apparatuses 6 for sucking the formed gas formed under the catalyst S, nine measuring instruments 7 for outputting signals according to the kind and concentration of the formed gas, and a calculating unit 8 for receiving the output signals from the measuring instrument 7 and identifying the kind of the formed gas and calculating the concentration thereof.

The reaction vessel 2 has a sealed structure to prevent leakage or the formed gas which leads intrusion of air and lowering of the analysis precision. For the uniform contact of a reactant gas with the nine catalysts S, each of the side walls of the reaction vessel 2 is provided with a supply pipe 3 of stainless steel for supplying a reactant gas into the reaction vessel 2, which communicates with the inside of the reaction vessel 2. Fixed to the bottom wall inside the reaction vessel 2 is a hot plate 4, on which is placed a holder plate 41 which can be inserted into and taken out from the reaction vessel 2. On the holder plate 41, there are arranged nine catalysts S to be evaluated, at a distance to form a matrix. In the present embodiment, the holder plate 41 has a flat top face, but it may be so arranged to have recesses at the positions for placing catalysts S to prevent displacement of the catalysts on the holder plate at the time of insertion and/or extraction of the holder plate The nine suction apparatuses 6 are each provided with a stainless steel suction pipe 61 for accommodating the formed gas inside and a pump 62 situated intermediately at the suction pipe 61, for sucking the formed gas. Each of the suction pipes 61 is partly inserted into the reaction vessel 2 through the opening provided on the top wall of the reaction vessel 2 with its end positioned directly above a catalyst S.

The nine measuring instruments 7 are combined with the end of each suction pipe 61 outside the vessel 2, so that the formed gas is introduced inside the measuring instruments 7 through the pipes 61. The measuring instruments 7 are respectively provided with three gas sensors 71 which detect different kinds of gases to each other The gas sensors 71 of this embodiment are a semiconductor type which changes the electric conductivity when the oxide semiconductor surface react with a specific gas.

The gas sensor to be used for the performance evaluation apparatus of the present invention is not limited to this type but may be of an electrochemical gas sensor, such as a potentiometric sensor, for measuring the electric current produced under the electric decomposition of gas, or for measuring the electric power produced by the contact with gas. In case the formed gas is various kinds of organic substance, carbon monoxide, carbon dioxide, etc., the apparatus may be an infrared type gas sensor which is a compact spectrochemical analyzer made by utilizing the characteristics that these gases absorb the infrared rays of specified wavelength. Alternatively, the sensor may be a quartz crystal oscillator type gas sensor which is formed of an oscillator comprising a quartz crystal oscillator coated with a film which adsorbs selectively a specific gas, so that, when a gas is adsorbed to the gas selective adsorption film, the oscillator changes the oscillation frequency according to the amount of adsorption. The measuring instruments 7 may be constituted by a plurality of the same kind of gas sensors as in the present embodiment, or by a plurality of the different kinds of gas sensors.

The measuring instruments 7 are connected to the stainless steel discharge pipes 63 for discharging the formed gases after measurement. In this embodiment, nine suction apparatuses 6 and nine measuring instruments 7 are provided for the evaluation of nine catalysts S at a time However, the number of the suction apparatuses and measuring instruments may be changed according to the number of the catalyst S. The number of the gas sensors 71 furnished on each measuring instrument 7 may be optionally selected according to the kind of the produced gas or the necessary analysis precision.

The calculating unit 8 receives output signals from the nine measuring instruments 7 sequentially selecting the cables 72 to identify the kind of the produced gas and calculate the concentrations thereof. Accordingly, the unit can perform evaluation of the performance of the nine catalysts S concurrently. The calculating unit 8 in this embodiment comprises a personal computer incorporated with a software for controlling the signal inputs and the pattern matching which is to be described later, and with an interface board having connected to the cables 72. Alternatively, the calculating unit 8 may be constituted as an exclusive unit.

Next, a method for using the catalyst performance evaluation apparatus 1 is explained. The explanation is given on the evaluation of the catalyst in the hydrogenation reaction for producing methanol by a reaction of carbon monoxide and hydrogen under the presence of a catalyst. In this case, each measuring instrument 7 is equipped, for example, with three different semiconductor gas sensors 71 which can mainly detect methanol, methane, and carbon monoxide. Before carrying out evaluation of the catalyst performance, under the condition where no catalyst is set in the vessel 2, a gas whose kind and concentration are known is supplied through the supply pipe 3. The gas to be supplied is selected from the same kind of gases as the formed gas (methanol, methane) formed under catalyst and the reactant gas (carbon monoxide, hydrogen). The gas supplied into the vessel 2 is sucked into the suction pipe 61 and led to the measuring instrument 7. After the air which had initially been filled in the vessel is discharged through the discharge pipe 63, the output signals from the measuring instruments 7 are sequentially taken into the calculating unit 8, and the calculated results are stored. The stored values are used for the pattern matching to be described later. The similar operations described above are repeated changing the kind of gas to be supplied, and, if necessary, changing concentration of the gas. In the present embodiment, the output values of the measuring instrument 7 are made in respect of known gases by using the catalyst performance evaluation apparatus 1 and stored, but alternatively the output values of the measuring instrument 7 in respect of known gases may be taken from other means beforehand and stored in the calculating unit 8.

Next, evaluation of catalyst is performed. In the hydrogenation reaction, superior catalysts form reaction from a lower temperature, produce much methanol, and less methane. First, nine catalysts S to be evaluated are arranged on the holder plate 41 and placed on the hot plate 4 in the vessel 2.

Next, a mixture of carbon monoxide gas and hydrogen gas is supplied to the vessel 2 through the supply pipes 3, and the temperature of the hot plate 4 is raised by the temperature regulator 5. Since any of the nine catalysts S does not cause reaction until they reach their own specific temperatures, carbon monoxide and hydrogen are sucked into the measuring instrument 7. Accordingly, at this stage, the outputs of the gas sensors 71 which can mainly detect the carbon monoxide become high. When some catalysts S reached a certain temperature where the hydrogenation reaction comes to be started, methanol and methane are formed, and then the outputs of the gas sensors which can mainly detect methanol and the gas sensors 71 which can mainly detect methane become high. Accordingly, by checking measuring instruments 7 which have a gas sensor 71 making high output, it is possible to identify the catalysts which have started hydrogenation reaction out of the nine catalysts S and to know the temperature at such time. The output signal of the temperature regulator 5 can be input into the calculating unit 8, so that the above temperature is automatically stored.

Regarding the hydrogenation reaction, identification of the formed methanol and methane and calculation of those concentrations can be achieved by comparing the pattern of the output values of the gas sensors 71 generated in the measurement of the formed gas ,with the patterns of the output values of the gas sensors generated in the measurement of the gases the kinds and concentrations of which are preliminary measured and stored.

Figure 2:
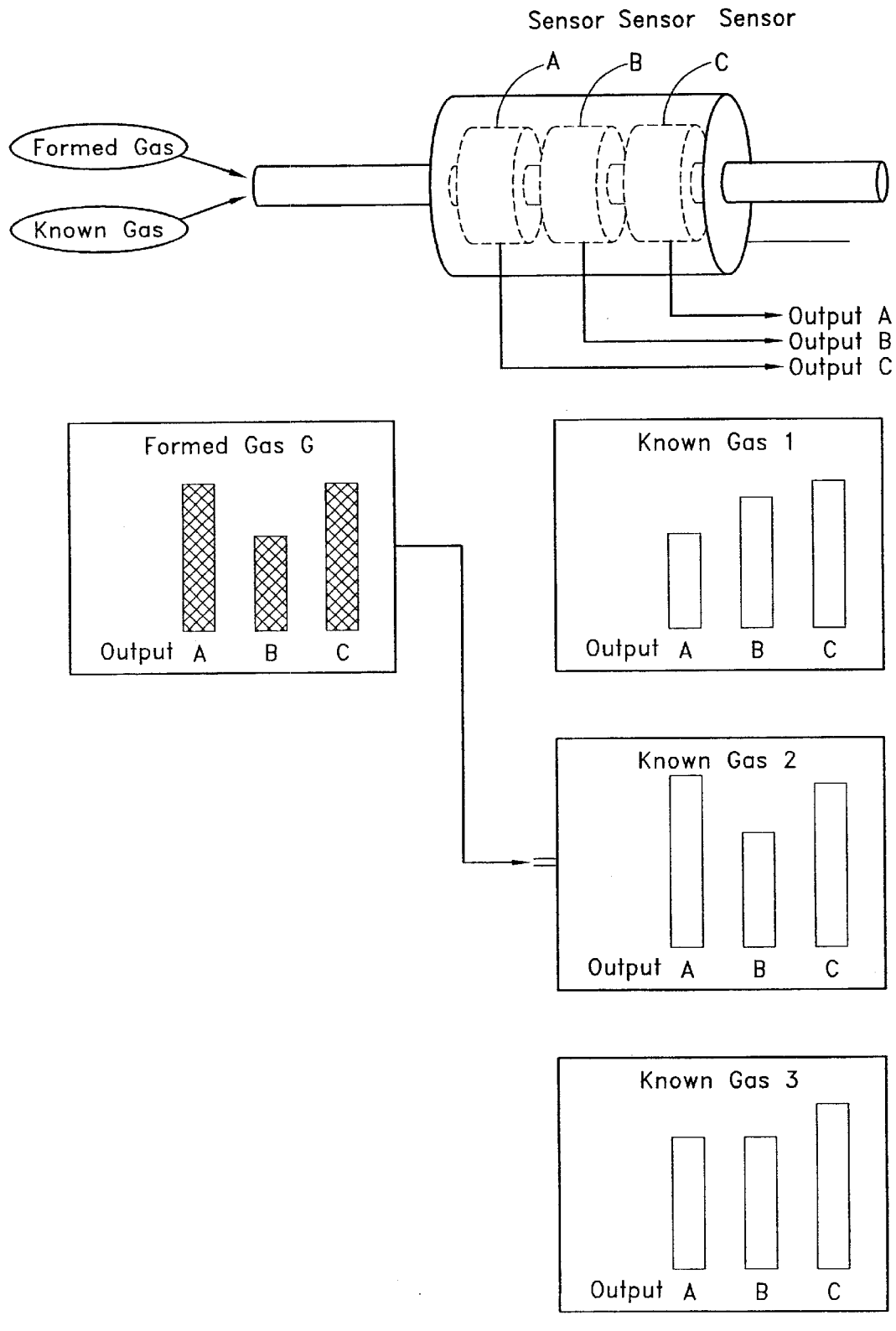
FIG. 2 shows graphs of the outputs of the sensors for explaining concept of the identification of the kind of the formed gas and calculation of concentration thereof.

FIG. 2 shows the concept of the steps for identification of the kind of the formed gas and calculation of the concentration. As shown in FIG. 2, an appropriate numbers of patterns formed by the output values of a set of the gas sensors 71 are stored in respect of the gases whose kinds and concentrations are known ("known gas 1", "known gas 2", "known gas 3", . . . in FIG. 2). The pattern formed by the output of the set of the gas sensors 71 generated in the measurement of the formed gas ("formed gas G" in FIG. 2), is compared with the stored patterns of the known gases. By evaluating the approximation between the measured and stored patterns and absolute values of the output, the kind of the formed gas is identified and concentration thereof is calculated. In the illustrated example, the pattern of the output of the formed gas is proximate to the pattern of the known gas 2, and thus the formed gas is identified as the gas of the same kind as the known gas 2. Also, from the comparison of the absolute values of A, B, and C in the pattern of the known gas 2 with the pattern of the formed gas, the ratio of the formed gas concentration to the known gas concentration is obtained. Accordingly, if the concentration of the known gas is previously known, the concentration of the formed gas can be obtained. With respect to the method for evaluating the approximation of the patterns, signal processing technique such as neural network or statistical procedure can be applied.

In this embodiment, description has been given on the hydrogenation reaction of carbon monoxide and hydrogen under catalyst for the production of methanol. However, besides this, the catalyst evaluating apparatus of the present invention can be used, for example, for catalyst evaluation in the oxidation reaction of propane and oxygen under catalyst for the production of acrolein or acrylic acid which is a useful chemical substance. In this case, good catalyst shows reaction from a lower temperature, forms much acrolein or acrylic acid, and forms less carbon monoxide or carbon dioxide. Furthermore, regarding a heat source, the present invention apparatus can be used for evaluation of catalyst for combustion in which methane is burnt under a catalyst to form carbon dioxide and water. In this case, good catalyst starts combustion at a lower temperature.

What is claimed is:

1. An apparatus for evaluating catalyst performance comprising:

a vessel in which a plurality of catalysts are disposed at a distance from each other;

a supply device for supplying a reactant gas into the vessel;

a plurality of measuring instruments provided with at least one gas sensor for each of the catalysts, each gas sensor sensing the formed gas individually by the contact of the reactant gas with the catalysts, and outputting signals according to the kind and concentration of the formed gas;

a calculating unit for identifying the kind of the formed gas and calculating the concentration thereof based on the output signal of the plurality of the measuring instruments; and a plurality of suction apparatuses, provided in the vicinity of each of the plurality of catalysts, for sucking the formed gas and leading the formed gas to the measuring instruments.

2. The apparatus for evaluating catalyst performance according to claim 1, wherein the plurality of measuring instruments are respectively provided with a plurality of gas sensors, and the calculating unit calculates the concentration of the formed gas by comparing the output values of the gas sensors taken by a preliminary measurement of a plurality of gases whose kinds and concentrations are known, with the output values of the gas sensors taken by a measurement of the formed gas.

3. The apparatus for evaluating catalyst performance according to claim 1, wherein the plurality of measuring instruments are respectively provided with a plurality of gas sensors, and the calculating unit identifies the kinds of the formed gas and calculates the concentration thereof by comparing the patterns of output values of the gas sensors taken by a preliminary measurement of a plurality of gases whose kinds and concentrations are known, with the patterns of output values of the gas sensors taken by a measurement of the formed gas.

* * * * *

UNITED STATES PATENT AND TRADEMARK OFFICE
CERTIFICATE OF CORRECTION

PATENT NO.    : 6,495,105 B1
DATED         : December 17, 2002
INVENTOR(S)   : Yusuke Yamada, Atsushi Ueda and Tetsuhiko Kobayashi It is certified that error appears in the above-identified patent and that said Letters Patent is hereby corrected as shown below:

<u>Title page,</u>
Item [73], should read:

-- [73] Assignee: Secretary, Agency of Industrial Science and Technology, Tokyo (JP) --

Signed and Sealed this

Twenty-seventh Day of May, 2003

JAMES E. ROGAN
*Director of the United States Patent and Trademark Office*